(12) United States Patent
Ogawa

(10) Patent No.: US 9,180,206 B2
(45) Date of Patent: Nov. 10, 2015

(54) PHARMACEUTICAL PREPARATION AND MANUFACTURING METHOD THEREOF

(75) Inventor: Kazufumi Ogawa, Awa (JP)

(73) Assignee: EMPIRE TECHNOLOGY DEVELOPMENT LLC, Wilmington, DE (US)

( * ) Notice: Subject to any disclaimer, the term of this patent is extended or adjusted under 35 U.S.C. 154(b) by 1068 days.

(21) Appl. No.: 12/600,002

(22) PCT Filed: May 14, 2007

(86) PCT No.: PCT/JP2007/060297
§ 371 (c)(1),
(2), (4) Date: Nov. 13, 2009

(87) PCT Pub. No.: WO2008/139637
PCT Pub. Date: Nov. 20, 2008

(65) Prior Publication Data
US 2011/0177057 A1    Jul. 21, 2011

(51) Int. Cl.
| A61K 31/43 | (2006.01) |
| A61K 47/48 | (2006.01) |
| A61K 41/00 | (2006.01) |
| H01F 1/00 | (2006.01) |
| B82Y 25/00 | (2011.01) |

(52) U.S. Cl.
CPC .......... *A61K 47/48861* (2013.01); *A61K 31/43* (2013.01); *A61K 41/00* (2013.01); *B82Y 25/00* (2013.01); *H01F 1/0054* (2013.01)

(58) Field of Classification Search
CPC . A61K 31/43; A61K 41/00; A61K 47/48861; H01F 1/0054; B82Y 25/00
USPC .................................................. 424/9.3, 9.32
See application file for complete search history.

(56) References Cited

U.S. PATENT DOCUMENTS

| 4,554,088 | A |  | 11/1985 | Whitehead et al. |
| 5,610,274 | A | * | 3/1997 | Wong ............................ 530/334 |
| 5,849,369 | A |  | 12/1998 | Ogawa |
| 2007/0140974 | A1 | * | 6/2007 | Torres et al. ............... 424/9.323 |

FOREIGN PATENT DOCUMENTS

| CA | 1000687 | * | 11/1976 | ............. C12N 11/10 |
| JP | 10-083913 |  | 3/1998 | |
| JP | 2007-137793 |  | 6/2007 | |
| WO | 9102811 A1 |  | 3/1991 | |
| WO | 96/02060 |  | 1/1996 | |
| WO | 03/066644 A1 |  | 8/2003 | |
| WO | WO 2004/049800 | * | 6/2004 | ............. A01N 25/08 |

OTHER PUBLICATIONS

Pan et al., Anal. Bioanal. Chem., 2007, 388, p. 279-286.*
Lin, Pol. Adv. Technol., 2001, 12, p. 285-292.*
Gmelin Handbuch der anorganischen Chemie, (GMELIN Handbook of Inorganic Chemistry), System No. 59, Verlag Chemic GmbH, Weinheim, Germany, p. 59 (1959).
Kobayashi, H., and Matsunaga, T., "Amino-silane modified superparamagnetic particles with surface-immobilized enzyme," Journal of Colloid and Interface Science, vol. 141, No. 2, Elsevier Inc., pp. 505-511 (1991).
Tiefenauer, L.X., et al., "Antibody-magnetite nanoparticles: In vitro characterization of a potential tumor specific contrast agent for magnetic resonance imaging," Bioconjugate Chem., vol. 4, No. 5, pp. 347-352 (1993).
International Search Report for International Application No. PCT/JP2007/060297 mailed on Aug. 21, 2007.

* cited by examiner

*Primary Examiner* — Michael G Hartley
*Assistant Examiner* — Leah Schlientz
(74) *Attorney, Agent, or Firm* — Workman Nydegger

(57) ABSTRACT

This invention provides a pharmaceutical preparation for DDS containing a pharmaceutical agent fixed by bonding to a monomolecular layer that is covalently bonded to a magnetic particle surface, (a) by reacting an alkoxysilane compound with the magnetic microparticle surface by dispersing a magnetic microparticle in a liquid mixture including an epoxy-containing alkoxysilane compound, a silanol condensation catalyst, and a non-aqueous organic solvent; (b) by washing the microparticle surface with an organic solvent to remove remaining surplus alkoxysilane compound for producing an epoxy-containing monomolecular layer that is covalently bonded to the microparticle surface; and (c) by fixing an imino-containing pharmaceutical agent such as a protein, amino acid, enzyme, antibody, antibiotic, antimicrobial, or contrast medium by reaction with the epoxy group.

20 Claims, 1 Drawing Sheet

PHARMACEUTICAL PREPARATION AND MANUFACTURING METHOD THEREOF

CROSS-REFERENCE TO RELATED APPLICATION

This Application is a U.S. National Stage filing under 35 U.S.C. 0371 of PCT Application No. PCT/JP2007/060297 filed on May 14, 2007.

BACKGROUND

To reduce or alleviate adverse drug reactions, a plurality of medication systems have been developed in which drugs are designed to exert the effect at a specific site at a designated timing (e.g., Japanese Unexamined Patent Application Nos. 2002-500177, 2000-503763, and 09-328438).

SUMMARY

Now, magnetically sensitive particles can be used for separation of a target substance by magnetic force. Manufacturing methods have been developed in order to produce a magnetically sensitive particle. Also, pharmaceutical preparations can include a magnetically sensitive particle for use in a medication system that can provide concentrated drug delivery to a specific site by magnetic force. In one embodiment, magnetically sensitive particles can be concentrated or separated from a mixture by magnetic force. The magnetically sensitive particles can be used for efficient separation of target substances, such as catalysts. Also, the magnetically sensitive particles can include pharmaceutical agents and can be used in pharmaceutical preparations for DDS that enable concentrated delivery of a drug to a specific site of a living organism (and administration of the drug at a reduced amount). Adverse drug reactions can be alleviated or the dose of the drug can be reduced by selective delivery with a magnetically sensitive particle.

In one embodiment, a magnetically sensitive particle can include a functional substance fixed to the particle by being bonded to an organic layer that is covalently bonded to a surface of the particle.

In one embodiment, the magnetically sensitive particle can include an organic layer that is a monomolecular layer.

In one embodiment, the magnetically sensitive can include a monomolecular layer covalently bonded to the surface of the particle. The monomolecular layer can include a substance having an epoxy group at one part, and another part bound to the magnetic microparticle surface via Si covalent bonding.

In one embodiment, a magnetically responsive pharmaceutical preparation can include a drug fixed to a magnetically responsive particle by bonding to an organic layer that is covalently bonded to a magnetic microparticle surface.

In one embodiment, the magnetically responsive pharmaceutical preparation can include a monomolecular organic layer.

In one embodiment, the magnetically responsive pharmaceutical preparation can include a magnetically responsive particle having a monomolecular layer covalently bonded to its surface, which monomolecular layer can include a compound having an epoxy group at one part and another part bound to the magnetic microparticle surface by Si covalent bonding.

In one embodiment, a method for manufacturing a magnetically sensitive particle can include:

(a) a step for reacting an alkoxysilane compound with a magnetic microparticle surface by dispersing a magnetic microparticle in a liquid mixture prepared by mixing, at least, an epoxy-containing alkoxysilane compound, a silanol condensation catalyst, and a non-aqueous organic solvent;

(b) a step of washing the microparticle surface with an organic solvent to remove remaining surplus alkoxysilane compound for producing an epoxy containing monomolecular layer that is covalently bonded to the microparticle surface; and (c) a step for binding a functional substance via the epoxy group.

In one embodiment, a method for manufacturing the magnetic microparticle can include a ketimine, organic acid, aldimine, enamine, oxazolidine, or aminoalkylalkoxysilane compound being used as a silanol condensation catalyst.

In one embodiment, a method for manufacturing the magnetic microparticle can include at least one cocatalyst compound selected from the group of ketimines, organic acids, aldimines, enamine, oxazolidines, and aminoalkylalkoxysilane compounds, which can be is used in addition to the silanol condensation catalyst.

In one embodiment, a method for manufacturing a magnetically responsive pharmaceutical preparation can include;

(a) a step for reacting an alkoxysilane compound with a magnetic microparticle surface by dispersing a magnetic microparticle in a liquid mixture prepared by mixing, at least, an epoxy-containing alkoxysilane compound, a silanol condensation catalyst, and a non-aqueous organic solvent; and (b) a step of washing the microparticle surface with an organic solvent to remove remaining surplus alkoxysilane compound for producing an epoxy-containing monomolecular layer that is covalently bonded to the microparticle surface.

In one embodiment, a method for manufacturing the magnetically responsive pharmaceutical preparation can include attaching an imino-containing drug to the microparticle surface after the step for producing the epoxy-containing monomolecular layer.

In one embodiment, a method for manufacturing the magnetically responsive pharmaceutical preparation can include a ketimine, organic acid, aldimine, enamine, oxazolidine, or aminoalkylalkoxysilane compound being used as a silanol condensation catalyst.

In one embodiment, a method for manufacturing the magnetically responsive pharmaceutical preparation can be at least one cocatalyst compound selected from the group of ketimines, organic acids, aldimines, enamines, oxazolidines, and aminoalkylalkoxysilane compounds being used in addition to the silanol condensation catalyst.

In one embodiment, the method for manufacturing the magnetically responsive pharmaceutical preparation can include coupling an imino-containing agent to the particle which the imino-containing agent is a drug, protein, amino acid, enzyme, antibody, antibiotic, antimicrobial, or contrast medium.

In one embodiment, a magnetically sensitive particle can be prepared to include a functional substance bound onto the surface via an organic layer that is covalently bonded to the magnetic microparticle surface. The preparation of the magnetically sensitive particle can include:

(i) a step for reacting an alkoxysilane compound with a magnetic microparticle surface by dispersing a magnetic microparticle in a liquid mixture prepared by mixing, at least, an epoxy-containing alkoxysilane compound, a silanol condensation catalyst, and a non-aqueous organic solvent;

(ii) a step for producing a epoxy-containing monomolecular layer that is covalently bonded to the microparticle surface by washing the microparticle surface with an organic solvent to remove remaining surplus alkoxysilane compound; and (iii) a step for binding a functional substance via the epoxy group.

In one embodiment, the magnetically sensitive particle can include a functional substance within a monomolecular organic layer, which retains the characteristics of the functional substance. Another embodiment can include the monomolecular layer being covalently bound to the surface and including a substance having an epoxy group at one part and another part that binds to the magnetic microparticle surface by Si covalent bonding. The epoxy group can be used for covalently bonding the functional substance to the magnetically sensitive particle. In another embodiment, a ketimine, organic acid, aldimine, enamine, oxazolidine, or aminoalkylalkoxysilane compound can be used as or in place of the silanol condensation catalyst, with a shortened manufacturing time. In another embodiment, at least one cocatalyst compound selected from the group of ketimines, organic acids, aldimines, enamines, oxazolidines, and aminoalkylalkoxysilane compounds can be used in addition to the silanol condensation catalyst, with a shortened manufacturing time.

A magnetically responsive pharmaceutical preparation can include a drug fixed to the particle by bonding to an organic layer that is covalently bonded to the microparticle surface. The preparation can include:

(a) a step for reacting an alkoxysilane compound with the magnetic microparticle surface by dispersing the magnetic microparticle in a liquid mixture prepared by mixing, at least, an epoxy-containing alkoxysilane compound, a silanol condensation catalyst, and a non-aqueous organic solvent; and (b) a step of washing the microparticle surface with an organic solvent to remove remaining surplus alkoxysilane compound for producing an epoxy-containing monomolecular layer that is covalently bonded to the microparticle surface.

In one embodiment, the organic layer can be a monomolecular organic layer that includes a functional substance where the organic layer retains the characteristics of the functional substance. In another embodiment, the monomolecular layer that is covalently bonded to the surface of the particle can include a substance having an epoxy group at one part and another part bound to the magnetic microparticle surface by Si covalent bonding. The epoxy group can be used for covalently binding the functional substance. For example, an imino-containing drug can be fixed onto the microparticle surface through the epoxy-containing monomolecular layer, which provides secure fixation of the drug to the particles. In another embodiment, a ketimine, organic acid, aldimine, enamine, oxazolidine, or aminoalkylalkoxysilane compound can be used as a silanol condensation catalyst, which catalyst can shorten the manufacturing time. In another embodiment, at least one cocatalyst compound selected from the group of ketimines, organic acids, aldimines, enamines, oxazolidines, and aminoalkylalkoxysilane compounds can be used in addition to the silanol condensation catalyst, which cocatalyst can provide an even shorter manufacturing time. In another embodiment, an imino-containing agent such as a protein, amino acid, enzyme, antibody, antibiotic, antimicrobial, or contrast medium, can be attached to the particle through the epoxy group.

As illustrated above, a magnetically sensitive particle can be concentrated or separated from a mixture by magnetic force, whereby an efficient separation of substances, such as a catalyst, can be achieved.

A pharmaceutical preparation for DDS can include a drug fixed to a magnetic microparticle surface without a significant reduction in the drug's action. The particle and drug can be concentrated to a target site by magnetic force after administered to humans, thereby exerting a particular effect for reducing the dosing amounts or attenuating adverse drug reactions of the drug.

BRIEF DESCRIPTION OF THE FIGURES

The foregoing aspects and many of the attendant advantages of the magnetically sensitive particles will become more readily appreciated as the same becomes better understood by reference to the following detailed description, when taken in conjunction with the accompanying drawings, wherein like reference numerals refer to like parts throughout the various views unless otherwise specified:

FIG. 1 schematically illustrates a magnetic microparticle reaction.

DETAILED DESCRIPTION

Figure 1A:
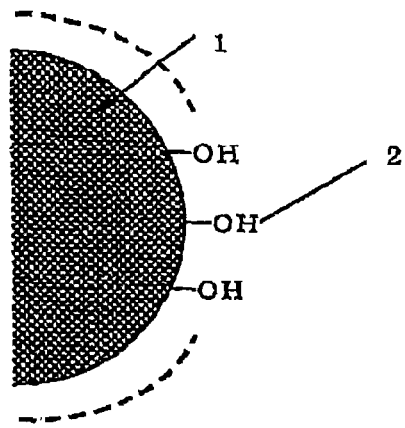
FIG. 1A presents a pre-reaction condition of a magnetic microparticle surface.

A magnetically sensitive particle can be used in biological applications. Also, the magnetically sensitive particle can be included in a pharmaceutical preparation. A magnetically sensitive particle can be used for separating a target substance from a mixture by a magnet when a functional substance is fixed in an organic layer that is covalently bonded to a surface of the magnetic microparticle. The magnetically responsive particle can be included in a pharmaceutical preparation that can be employed for a drug delivery system (DDS), to deliver an active drug substance specifically to a target site. The magnetic particle allows for controlled delivery and timed delivery.

A 'magnetically responsive pharmaceutical preparations for DDS' can include preparations in which an imino-containing drug, such as a protein, amino acid, enzyme, antibody, antibiotic, antimicrobial, or contrast medium, is fixed on a surface of a magnetic microparticle.

A magnetically sensitive particle can include a functional substance that is bonded to an organic layer that is covalently bonded to a magnetic microparticle. The particle can be prepared by:

(a) a step for reacting an alkoxysilane compound with a magnetic microparticle surface by dispersing a magnetic microparticle in a liquid mixture prepared by mixing, at least, an epoxy-containing alkoxysilane compound, a silanol condensation catalyst, and a non-aqueous organic solvent;

(b) a step of washing the microparticle surface with an organic solvent to remove remaining surplus alkoxysilane compound for producing an epoxy-containing monomolecular layer that is covalently bonded to the microparticle surface; and (c) a step for binding a functional substance via the epoxy group.

A pharmaceutical preparation for DDS can include a drug or agent fixed to the particle by bonding to a monomolecular layer that is covalently bonded to a magnetic microparticle surface. The particle can be prepared by:

(i) reacting an alkoxysilane compound with the magnetic microparticle surface by dispersing a magnetic microparticle in a liquid mixture prepared by mixing, at least, an epoxy-containing alkoxysilane compound, a silanol condensation catalyst, and a non-aqueous organic solvent;

(ii) producing an epoxy-containing monomolecular layer that is covalently bound to the microparticle surface by washing the microparticle surface with an organic solvent to remove remaining surplus alkoxysilane compound; and (iii) fixing an imino-containing drug or agent, such as a protein, amino acid, enzyme, antibody, antibiotic, antimicrobial, or contrast medium, onto the magnetic microparticle surface.

The magnetically sensitive particles can be employed for an efficient separation of substances used as a catalyst or for other purposes.

The pharmaceutical preparations by being concentrated to a target site by magnetic force after administered to humans can have excellent effects for reducing the dosing amounts without reducing the drug's therapeutic actions or attenuating adverse drug reactions.

The particle will now be further illustrated with reference to specific embodiments, though the particle should not be construed as limited to the details shown.

Figure 1B:
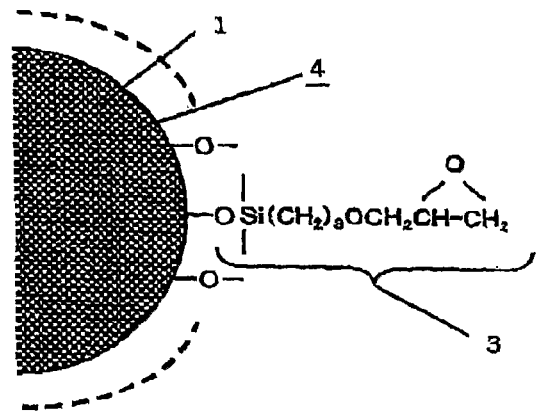
FIG. 1B presents a formation of an epoxy-containing monomolecular layer.
Figure 1C:
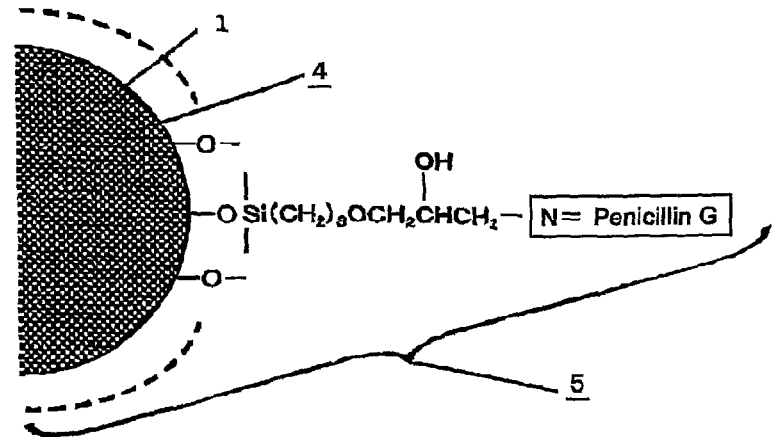
FIG. 1C presents penicillin G fixation by bonding.

Magnetically sensitive particles can include a catalyst or a coagulant as a functional substance. The magnetically responsive particle can be included in pharmaceutical preparations. The particle can be linked to an imino-containing drugs or agents, such as proteins, amino acids, enzymes, antibodies, antibiotics, antimicrobials, and contrast media, which can be fixed onto the surface of the magnetic microparticles. For example, a magnetic particle can include penicillin G as the functional substance. As shown in FIGS. 1A-1C, magnetically responsive particles can be prepared to include an agent. Dry magnetite particles (1) having a particle size of several ten nanometers were well dried. A chemical adsorbent can include an epoxy group at one part and an alkoxysilane group at another part. The epoxy and alkoxysilane can be functional groups, examples of which are shown in formula (C1) below. A silanol condensation catalyst can include dibutyltin diacetylacetonate. The chemical absorbent and silanol condensation catalyst can be weighed out in a weight percent of 99% and 1%, respectively. These compounds were then added to a silicone fluid, such as hexamethyldisiloxane, in a total weight percent of about 1% (preferably, in a weight percent range of 0.5%-3%) to prepare an adsorbent-containing mixture.

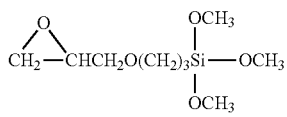

[C1]

The dry magnetite particles were added under stirring to the adsorbent-containing mixture to react at room temperature in ambient air (relative humidity: 45%) for about 2 hours. Under such conditions, the dry magnetite microparticles, which have a plurality of hydroxy groups on the surface thereof (FIG. 1A), underwent a dealcoholization reaction (in this example, demethanol reaction) with the —Si(OCH$_3$) group of the above-mentioned chemical adsorbent in the presence of silanol condensation catalyst to form a chemical bond as shown in the below formula (C2). This reaction yielded an epoxy-containing chemical adsorbent monomolecular layer (3) bonded to the magnetic microparticle surface with a thickness of about 1 nanometer (FIG. 1B).

Washing the microparticles under stirring with a chlorine-containing solvent, such as tichloroethylene, produced magnetite microparticles (4) covered with an epoxy-containing chemical adsorbent monomolecular layer.

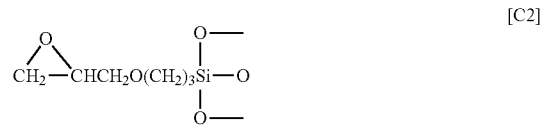

[C2]

This procedure did not substantially change the particle size, because the covering layer had a very thin thickness on the order of a nanometer.

When the microparticles were exposed to air without the washing treatment, the chemical adsorbent remaining on the microparticle surface reacted with moisture in the air as the solvent evaporated, and magnetite microparticles covered with a very thin organic polymer film comprising the above-mentioned chemical adsorbent with similar functionality were produced. The films caused no operational troubles or problems to after-treatment processes, and the resulting microparticles could be handled similarly to the monomolecular layer-covered magnetite microparticles.

A manufacturing method can include a dealcoholization reaction for acid-reacting substances, such as magnetite microparticles.

The magnetite microparticles (4) covered with an epoxy-containing chemical adsorbent monomolecular layer were dispersed in an alcohol medium with penicillin G, and the mixture was heated to react. Penicillin G, having an imino group close to the β-lactam ring, was fixed in a layered manner on the microparticle surface by addition reaction of the imino and epoxy groups, as shown in the following reaction formula (C3). Removal of unreacted penicillin G by washing produced a magnetically responsive pharmaceutical preparation (5) for DDS comprising surface-bound penicillin G (FIG. 1C).

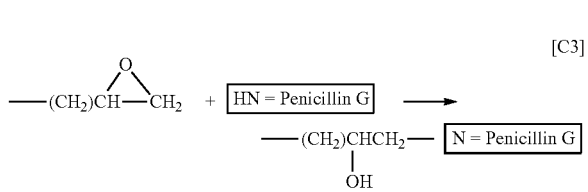

[C3]

A pharmaceutical preparation having particles with a diameter of several ten nanometers is unlikely to clog blood vessels when intravascularly administered dispersed in purified water. In addition, the pharmaceutical preparation can be attracted by magnetic force toward a magnet placed nearby. As such, the magnet can serve to concentrate the particles and drug to an affected area by placing a magnet near a desired area. A blood circulates the magnetically responsive particles can be attracted to the magnet within a certain period of time.

Accordingly, the magnetically responsive particles can provide an efficient therapeutic method whereby a high penicillin G concentration is attained in the vicinity of the affected area with a small amount of dose, thereby reducing adverse drug reactions.

This technique is applicable to any imino-containing drugs or agents, such as proteins, amino acids, enzymes, antibodies, antibiotics, antimicrobials, and contrast media. Typically, this technique can be applicable to cephalexin, or other agents having imino and amino groups.

Similar to the substance of formula (C1), other epoxy-containing chemical adsorbents can be used, such as substances (1) to (10):

$$(CH_2OCH)CH_2O(CH_2)_7Si(OCH_3)_3 \quad (1)$$

$$(CH_2OCH)CH_2O(CH_2)_{11}Si(OCH_3)_3 \quad (2)$$

$$(CH_2CHOCH(CH_2)_2)CH(CH_2)_2Si(OCH_3)_3 \quad (3)$$

$$(CH_2CHOCH(CH_2)_2)CH(CH_2)_4Si(OCH_3)_3 \quad (4)$$

$$(CH_2CHOCH(CH_2)_2)CH(CH_2)_6Si(OCH_3)_3 \quad (5)$$

$$(CH_2OCH)CH_2O(CH_2)_7Si(OC_2H_5)_3 \quad (6)$$

$$(CH_2OCH)CH_2O(CH_2)_{11}Si(OC_2H_5)_3 \quad (7)$$

$$(CH_2CHOCH(CH_2)_2)CH(CH_2)_2Si(OC_2H_5)_3 \quad (8)$$

$$(CH_2CHOCH(CH_2)_2)CH(CH_2)_4Si(OC_2H_5)_3 \quad (9)$$

$$(CH_2CHOCH(CH_2)_2)CH(CH_2)_6Si(OC_2H_5)_3, \quad (10)$$

wherein (CH$_2$OCH)— group designates a functional group shown by the following formula (C4), and (CH$_2$CHOCH(CH$_2$)$_2$)CH— group designates a functional group shown by the following formula (C5):

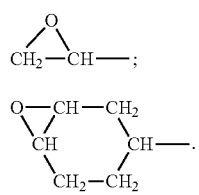

In one embodiment, metal carboxylates, carboxylic acid ester metal salt, metal carboxylate polymers, metal carboxylate chelates, titanic esters, and titanic ester chelates can be used as the silanol condensation catalyst. More specifically, tin (II) acetate, dibutyltin dilaurate, dibutyltin dioctate, dibutyltin diacetate, dioctyltin dilaurate, dioctyltin dioctate, dioctyltin diacetate, tin (II) dioctanoate, lead naphthenate, cobalt naphthenate, iron 2-ethylhexenate, dioctyltin bisoctylthioglycolic acid ester salt, dioctyltin maleic acid ester salt, dibutyltin maleic acid salt polymer, dimethyltin mercaptopropionic acid salt polymer, dibutyltin bis(acetylacetate), dioctyltin bis-acetyl laurate, tetrabutyltitanate, tetranonyltitanate, and bis(acetylacetonyl) di-propyltitanate can be used.

For the reaction medium, non-aqueous organic solvents with a boiling point in an approximate range of 50° C. to 250° C., such as chlorine-containing organic solvents, hydrocarbon solvents, fluorocarbon solvents, silicone solvents, dimethylformamide, or mixtures thereof, can be used. Besides these solvents, alcohol solvents, such as methanol, ethanol, or propanol, and mixtures thereof can be used for forming the organic film by evaporation of the solvent when the chemical adsorbent is an alkoxysilane compound.

Specific examples of a reaction medium can include chlorine-containing organic solvents, non-aqueous petroleum naphtha, solvent naphtha, petroleum ethers, petroleum benzine, isoparaffins, normal paraffins, decalins, industrial gasolines, nonane, decane, kerosene, dimethyl silicone, phenyl silicone, alkyl-modified silicone, polyether silicone, dimethylformamide, and mixtures thereof.

The fluorocarbon solvents can include chlorofluorocarbon solvents, Fluorinerts™ (produced by 3M Company), Afludes™ (manufactured by Asahi Glass Co., Ltd.). These solvents may be used singly or in combination if the solvents mix well. Chlorine-containing organic solvents such as chloroform may also be used.

When a ketimine, organic acid, aldimine, enamine, oxazolidine, or aminoalkylalkoxysilane compound was used as a condensation catalyst, the reaction time was reduced from one-half to two-thirds for similar reaction mixture concentrations.

Moreover, when a ketimine, organic acid, aldimine, enamine, oxazolidine, or aminoalkylalkoxysilane compound is used in addition to the silanol condensation catalyst (at a ratio to the catalyst ranging from 1:9 to 9:1, but preferably at a 1:1 ratio under ordinary conditions), the reaction time can be reduced several times (up to about 30 minutes), thereby shortening the total manufacturing time several times.

When, for example, dibutyltin oxide, a silanol catalyst, was replaced by H3, a ketimine compound, provided by Japan Epoxy Resins Co., Ltd. with all other conditions remaining the same, the results were similar with the exception that the reaction time was shortened to approximately one hour. Moreover, when the silanol catalyst was replaced by a mixture (1:1) of H3, a ketimine compound, provided by Japan Epoxy Resins Co., Ltd. and dibutyltin bis(acetylacetonate), a silanol catalyst, with all other conditions remaining the same, the results were similar with the exception that the reaction time was shortened to approximately 30 minutes.

Accordingly, these results indicated that ketimine, organic acid, aldimine, enamine, oxazolidine, and aminoalkylalkoxysilane compounds have higher catalytic activities than conventional silanol condensation catalysts.

It was also indicated that when a conventional silanol condensation catalyst was used together with a compound selected from the group consisting of ketimine, organic acid, aldimine, enamine, oxazolidine, and aminoalkylalkoxysilane compounds, the catalytic activity was enhanced. Usable ketimine compounds include, but are not limited to, 2,5,8-triaza-1,8-nonadiene, 3,11-dimethyl-4,7,10-triaza-3,10-tridecadiene, 2,10-dimethyl-3,6,9-triaza-2,9-undecadiene, 2,4,12,14-tetramethyl-5,8,11-triaza-4,11-pentadecadiene, 2,4,15,17-tetramethyl-5,8,11,14-tetraaza-4,14-octadecadiene, and 2,4,20,22-tetramethyl-5,12,19-triaza-4,19-trieicosadiene.

Usable organic acids include, but are not limited to, formic acid, acetic acid, propionic acid, butyric acid, and malonic acid, which provided similar results. Whereas a magnetite microparticle was employed for the purpose of illustration in the above embodiment, to the magnetite microparticles can be replaced with other magnetic or magnetically responsive microparticles or nanoparticles of any type or nature, as far as the particles include active hydrogen atoms, such as in hydroxy groups, on the surface thereof. Specifically, examples of the applicable magnetic microparticles can include magnetic metal microparticles, such as, for example, iron, chromium, nickel, or alloys thereof and magnetic metal oxide microparticles comprising, for example, ferrite, magnetite, or chromium oxide.

The invention claimed is:
1. A particle comprising:
   a magnetically sensitive particle;
   a first linker linked to the magnetically sensitive particle at one end and having an epoxy reaction product on the opposite end, the first linker being selected from the group consisting of (CH$_2$OCH)CH$_2$O(CH$_2$)$_2$Si(O)$_3$, (CH$_2$OCH)CH$_2$O(CH$_2$)$_{11}$Si(O)$_3$, (CH$_2$CHOCH

$(CH_2)_2)CH(CH_2)_2Si(O)_3$, $(CH_2CHOCH(CH_2)_2)CH(CH_2)_4Si(O)_3$, $(CH_2CHOCH(CH_2)_2)CH(CH_2)_6Si(O)_3$, wherein the epoxy reaction product has a structure of

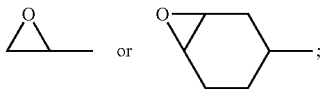

and
an agent having a terminal imino group linked to the epoxy reaction product opposite of the magnetically sensitive particle.

2. The particle of claim 1, comprising:
the magnetically sensitive particle having one or more active hydrogen groups; and
an alkylsilane linker linked to the particle through the active hydrogen group, said alkylsilane linker having the epoxy reactant product opposite of the active hydrogen group, the epoxy reactant product resulting from reacting an epoxide with a nitrogen group of the agent.

3. The particle of claim 2, wherein the epoxy reactant product results from reacting the epoxide with the terminal imino group of the agent.

4. The particle of claim 1, wherein the particle is a microparticle.

5. The particle of claim 1, wherein the particle is a nanoparticle.

6. The particle of claim 1, wherein the particle includes a metal or a metal oxide.

7. The particle of claim 1, wherein the particle includes iron, chromium, nickel ferrite, magnetite, alloys thereof, oxides thereof, or combinations thereof.

8. The particle of claim 1, wherein the agent is a protein, amino acid, enzyme, antibody, antibiotic, antimicrobial, contrast medium, or drug.

9. A composition comprising:
a plurality of particles, each particle comprising:
a magnetically sensitive particle;
a first linker linked to the magnetically sensitive particle at one end and having an epoxy reaction product on the opposite end, the first linker being selected from the group consisting of $(CH_2OCH)CH_2O(CH_2)_2Si(O)_3$, $(CH_2OCH)CH_2O(CH_2)_{11}Si(O)_3$, $(CH_2CHOCH(CH_2)_2)CH(CH_2)_2Si(O)_3$, $(CH_2CHOCH(CH_2)_2)CH(CH_2)_4Si(O)_3$, $(CH_2CHOCH(CH_2)_2)CH(CH_2)_6Si(O)_3$, wherein the epoxy reaction product has a structure of

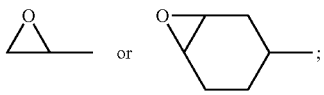

and
an agent having a terminal imino group selected from the group consisting of penicillin G and cephalexin linked to the epoxy reaction product opposite of the magnetically sensitive particle.

10. The composition of claim 9, comprising:
the magnetically sensitive particle having one or more active hydrogen groups; and
an alkylsilane linker linked to the particle through the active hydrogen group, said alkylsilane linker having the epoxy reactant product opposite of the active hydrogen group, the epoxy reactant product resulting from reacting an epoxide with a nitrogen group of the agent.

11. The composition of claim 10, wherein the epoxy reactant product results from reacting the epoxide with the terminal imino group of the agent.

12. The composition of claim 9, wherein the particle includes a metal or a metal oxide.

13. The composition of claim 9, wherein the particle includes iron, chromium, nickel ferrite, magnetite, alloys thereof, oxides thereof, or combinations thereof.

14. A method of manufacturing a magnetically sensitive particle, the method comprising:
providing a linker having an alkoxysilane at one and an epoxide group opposite of the alkoxysilane, the linker being selected from the group consisting of $(CH_2OCH)CH_2O(CH_2)_2Si(OCH)_3$, $(CH_2OCH)CH_2O(CH_2)_{11}Si(OCH_3)_3$, $(CH_2CHOCH(CH_2)_2)CH(CH_2)_2Si(OCH)_3$, $(CH_2CHOCH(CH_2)_2)CH(CH_2)_4Si(OCH_3)_3$, $(CH_2CHOCH(CH_2)_2)CH(CH_2)_6Si(OCH_3)_3$, $(CH_2OCH)CH_2O(CH_2)_7Si(OC_2H_5)_3$, $(CH_2OCH)CH_2O(CH_2)_{11}Si(OC_2H_5)_3$, $(CH_2CHOCH(CH_2)_2)CH(CH_2)Si(OC2H_5)_3$, $(CH_2CHOCH(CH_2)_2)CH(CH_2)_4Si(OC2H_5)_3$, $(CH_2CHOCH(CH_2)_2)CH(CH_2)_6Si(OC2H_5)_3$, wherein the epoxide group has a structure of

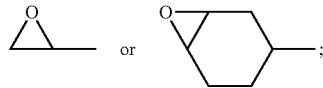

linking the linker to a magnetically sensitive particle through the alkoxysilane such that the epoxide group extends from the magnetically sensitive particle;
reacting the epoxide group with an agent having a terminal imino group to form an epoxy reaction product that links the agent to the linker.

15. The method of claim 14, comprising:
reacting an active hydrogen group of the magnetically sensitive particle with the alkoxysilane; and/or
reacting the epoxide group with the terminal imino group of the agent.

16. The method of claim 14, comprising:
dispersing the particle in a liquid mixture of the linker, a condensation catalyst, and a non-aqueous organic solvent; or
washing the particle with an organic solvent to remove surplus linker.

17. The method of claim 16, wherein the condensation catalyst is selected from a silanol condensation catalyst, ketamines, organic acids, aldimines, enamines, oxazolidines, aminoalkylalkoxysilanes, or combinations thereof.

18. The method of claim 14, wherein the agent is a protein, amino acid, enzyme, antibody, antibiotic, antimicrobial, contrast medium, or drug.

19. The particle of claim 1, wherein the agent is selected from the group consisting of penicillin G and cephalexin.

20. The method of claim 14, wherein the agent is selected from the group consisting of penicillin G and cephalexin.

* * * * *